United States Patent [19]

Oxford et al.

[11] Patent Number: 4,822,154
[45] Date of Patent: Apr. 18, 1989

[54] IMPROVEMENTS IN OR RELATING TO BORESCOPES

[75] Inventors: Colin G. Oxford, Canvey Island; George C. Parker, Westcliff-on-Sea; Roger L. Gray, Shoeburyness, all of United Kingdom

[73] Assignee: Keymed (Medical and Industrial Equipment Limited), Southend-on-Sea, England

[21] Appl. No.: 114,997

[22] Filed: Oct. 30, 1987

[30] Foreign Application Priority Data

Nov. 13, 1986 [GB] United Kingdom ............... 8627109

[51] Int. Cl.$^4$ .............................................. G02B 23/24
[52] U.S. Cl. ......................................... 350/572; 128/6; 350/573; 356/241
[58] Field of Search ..................... 350/252, 318–319, 350/506, 537, 540–544, 561–562, 572–577, 96.26; 356/241; 128/6

[56] References Cited

U.S. PATENT DOCUMENTS

| 689,220 | 12/1901 | Parrish | 350/574 |
| 737,844 | 9/1903 | Hubbard | 350/575 |
| 2,138,067 | 11/1938 | Mossberg | 350/562 |
| 2,453,862 | 11/1948 | Salisbury | 350/96.26 |
| 3,297,022 | 1/1967 | Wallace | 356/241 |
| 3,326,620 | 6/1967 | Marie | 350/573 |
| 4,148,551 | 4/1979 | MacAnally | 350/573 |
| 4,173,392 | 11/1979 | Ekinaka et al. | 350/96.26 |
| 4,616,631 | 10/1986 | Takahashi | 128/6 |

Primary Examiner—John K. Corbin
Assistant Examiner—Martin Lerner
Attorney, Agent, or Firm—Beveridge, DeGrandi & Weilacher

[57] ABSTRACT

An optical assembly 7, 8 providing an optical relay of a borescope 1 has a plurality of lenses 7 spaced apart by tubular spacers 8 through which the optical path extends. The spacers 8 include formations 9, 10 and 11 for connecting adjacent spacers and for housing the lenses 7 such that the spacers 8 and the lenses form a self supporting assembly. The optical assembly 7, 8 locates in a window tube 19 located within a tubular shaft 2 with a fibre optic bundle 16 occupying a duct 17 formed between the window tube and the shaft. The borescope 1 is convenient to assemble with minimum contamination and maximizes the optical path cross sectional area available.

9 Claims, 3 Drawing Sheets

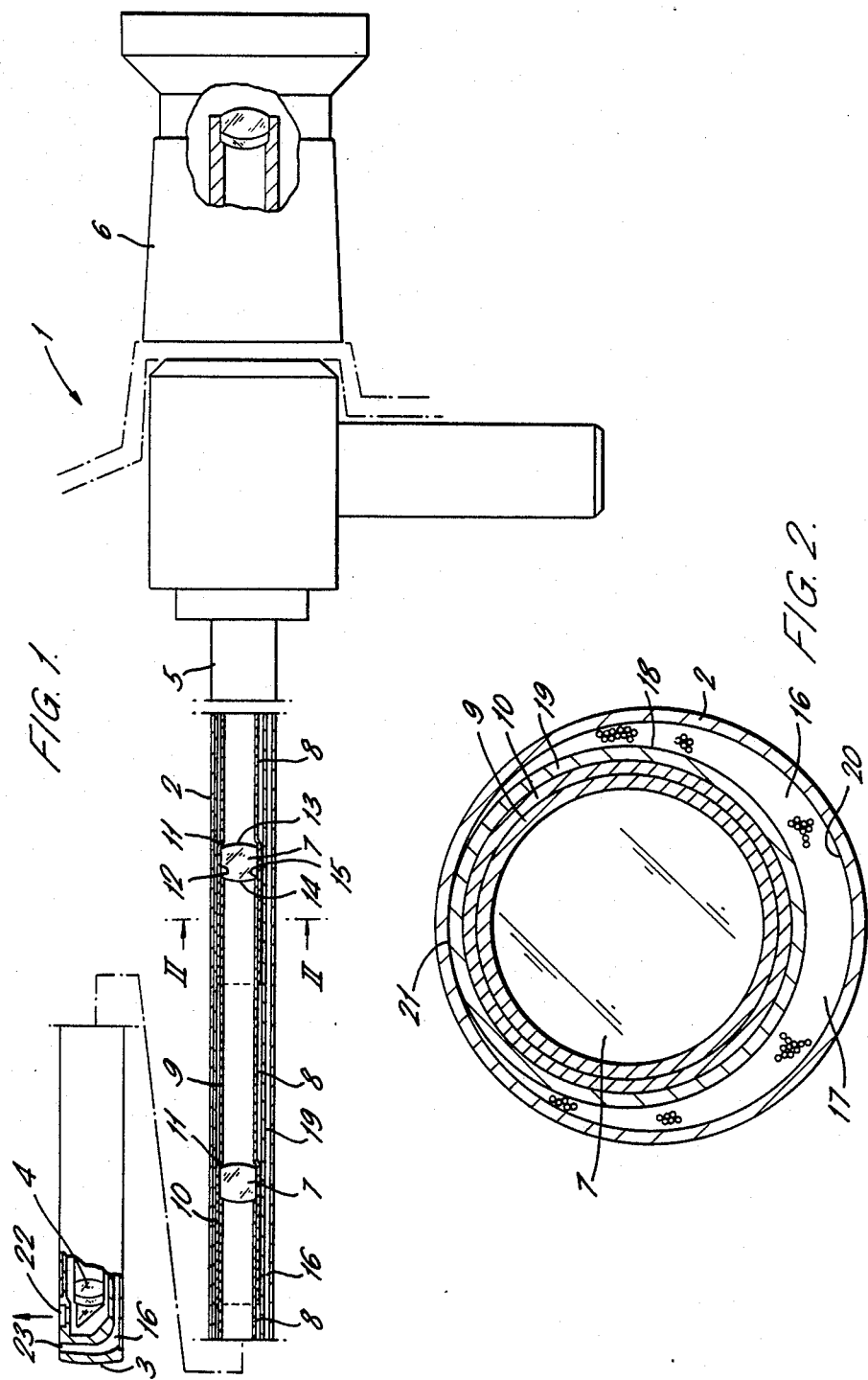

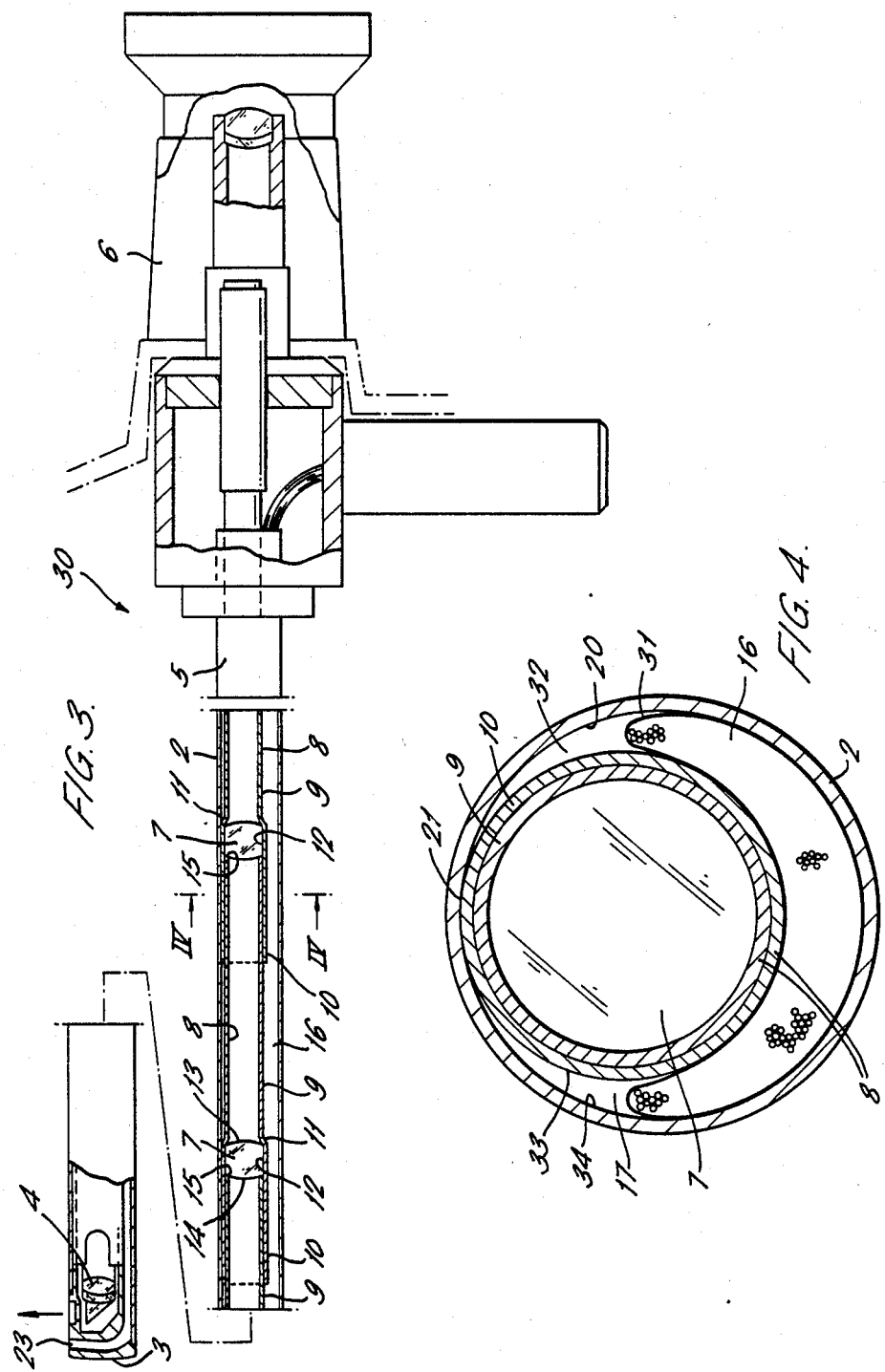

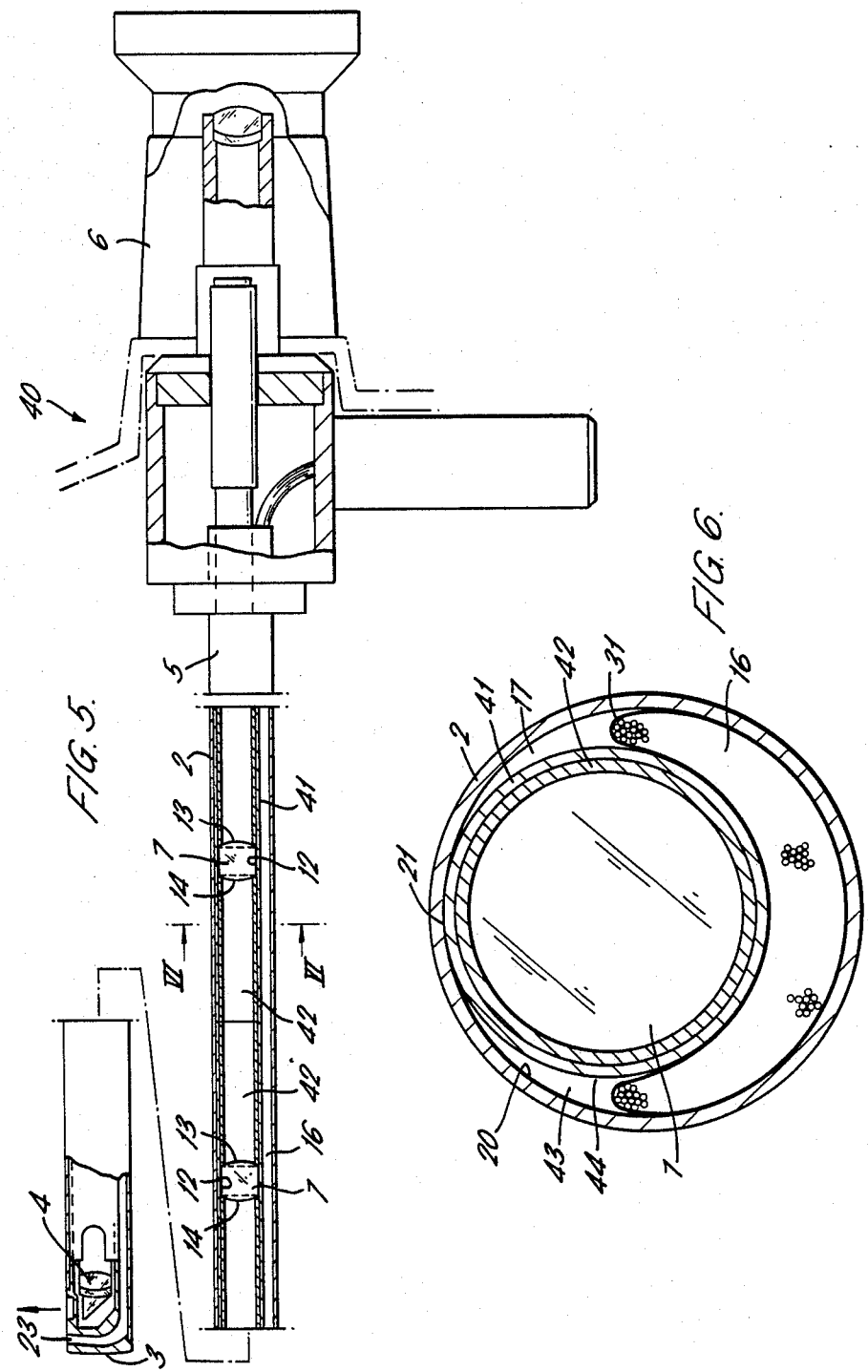

IMPROVEMENTS IN OR RELATING TO BORESCOPES

This invention relates to borescopes and to an optical assembly for use as an optical relay of an borescope.

Borescopes are known for use in through bore inspection of inaccessible objects and having a tubular shaft having a first end for insertion into the bore, an objective optical system at the first end of the shaft for viewing an object, an eye piece at the second end of the shaft and a fibre optic bundle for conducting light along the shaft from a light source to the first end of the shaft to illuminate the object. Such borescopes are also known to include an optical relay for relaying light from the objective system to the eye piece such that the object may be imaged in the eye piece. Such optical relays are known to comprise lenses which are housed in a lens tube and are spaced apart by tubular spacers through which the optical path extends. The lens tube is then a sliding fit within a window tube having a window through which the objective system may view the object and the window tube is in turn housed within the shaft such that the fibre optic bundle occupies a duct defined by the exterior surface of the window tube and the interior surface of the shaft.

In designing such a borescope the design criteria are generally to provide high resolution optics, high illumination of the object, high strength and rigidity and ease of serviceability. Whilst each of these attributes may be improved by increasing the cross sectional area or dimensions of components, for example by using larger lenses or more optical fibres, there is an overriding requirement that the external diameter of the shaft must be no more than the size of bore through which the shaft is to pass so that a compromise must be made in selecting the dimensions of the components.

A further problem with such borescopes, which are required to be manufactured in a variety of lengths, is that assembly requires lenses and spacer tubes to be slid into position within the lens tube and it has been found that such sliding produces contamination of the space contained within the optical assembly because of the scraping of parts during sliding. This contamination is greater as the borescope length is increased.

According to the present invention there is disclosed an optical assembly for use as an optical relay of a borescope in which a plurality of optical elements are spaced apart by tubular spacers through which the optical path extends wherein the spacers include formations for connecting adjacent spacers and for housing the optical elements such that the spacers and optical elements form a self supporting assembly.

An advantage of such an optical assembly is that the sliding of components is minimised during assembly and each tubular spacer is accessible for cleaning internally before assembly with the next optical element or spacer no matter what length of borescope is being assembled.

Preferably the formations comprise male and female portions of each spacer, which portions interfit with co-operating portions of adjacent spacers.

Preferably each spacer comprises a tube of substantially uniform wall thickness, the tube diameter being stepped at an annular shoulder such that a male portion is formed on one side of the shoulder and a female portion of larger diameter is formed on the other side of the shoulder, the external and internal diameters of the male and female portions respectively being such as to provide a sliding fit connection between cooperating portions of adjacent spacers.

According to a further aspect of the invention there is disclosed a borescope for use in through-bore inspection of inaccessible objects comprising a tubular shaft having a first end for insertion in use into a bore, objective means at the first end of the shaft for viewing an object, imaging means at the second end of the shaft, and optical relay means for relaying light from the objective means to the imaging means such that the object may be imaged by the imaging means wherein the relay means comprises an optical assembly as hereinbefore disclosed.

Preferably the borescope includes fibre optic means for conducting light along the shaft from a light source to the first end of the shaft to illuminate the object.

Advantageously the optical assembly is housed in a window tube having a window through which the objective means may view an object, the optical assembly is a sliding fit within the window tube and the fibre optic means occupies a duct defined by the exterior surface of the window tube and the interior surface of the shaft.

Conveniently the window tube may be in contact with one side of the shaft such that the duct is crescent shaped in cross section.

Alternatively the optical assembly may be housed in the shaft and the fibre optic means may occupy a duct defined by the external surface of the optical assembly and the internal surface of the shaft, which fibre optic means comprises a bundle of optical fibres in a flexible sheath.

Preferably the sheath is of a low friction material.

According to a further aspect of the invention there is disclosed a method of assembling a borescope having an optical assembly as hereinbefore disclosed comprising the steps of fitting an optical element into a female portion of a first spacer, fitting a male portion of a further spacer into the female portion of the first spacer together with an adhesive layer therebetween, fitting a further optical element into the female portion of the further spacer and adding additional further spacers and optical elements in like manner as required to form an optical assembly.

Preferably the method includes the further steps of cleaning each spacer internally before each step of fitting an optical element or further spacer therein.

According to a further aspect of the invention there is disclosed a borescope for use in through bore inspection of inaccessible objects comprising a tubular shaft having a first end for insertion in use into a bore, fibre optic means for conducting light along the shaft from a light souce to the first end of the shaft to illuminate the object, objective means at the first end of the shaft for viewing an object, imaging means at the second end of the shaft, and optical relay means for relaying light from the objective means to the imaging means such that the object may be imaged by the imaging means wherein the relay means comprises a lens tube within which a plurality of optical elements are maintained in spaced apart relationship by tubular spacers, which optical elements and spacers are slideably received within the lens tube, and wherein the fibre optic means comprises a bundle of optic fibres in a flexible sheath and occupies a duct defined by the external surface of the lens tube and the internal surface of the shaft.

Preferably the sheath is of a low friction material.
Conveniently the lens tube may be in contact with one side of the shaft such that the duct is crescent shaped in cross section.

Specific embodiments of the invention will now be described by way of example only and with reference to the accompanying drawings of which;

FIG. 1 is a part sectional view of a borescope having an optical assembly in accordance with the present invention housed in a window tube, FIG. 2 is a cross sectional view through the shaft of the borescope of FIG. 1, FIG. 3 is a part sectional view of a borescope having an optical assembly in accordance with the present invention and a fibre optic bundle contained in a flexible sheath, FIG. 4 is a sectional view through the shaft of the borescope of FIG. 3, FIG. 5 is a part sectional view of a borescope having a conventional optical assembly including a lens tube and having a fibre optic bundle contained in a flexible sheath in accordance with an aspect of the present invention, and FIG. 6 is a cross sectional view through the shaft of the borescope of FIG. 5.

The borescope 1 of FIGS. 1 and 2 comprises a tubular shaft 2 having a first end 3 housing an objective optical system 4 and having a second end 5 connected to an eye piece 6.

Lenses 7 are spaced apart along the length of the shaft 2 by spacers 8 such that the lenses and spacers together comprise an optical assembly 7, 8 which acts as an optical relay such that an object viewed by the objective optical system may be imaged in the eye piece.

Each spacer 8 has a male portion 9 and a female portion 10 which portions interfit with mating portions of adjacent spacers. Each spacer 8 is tubular and of substantially constant wall thickness along its length and is stepped in diameter at an annular shoulder 11 such that a male portion 9 is formed on one side of the shoulder and a female portion of larger diameter is formed on the other side of the shoulder. Interfitting male and female portions 9, 10 are a sliding fit with one another and are adhesively bonded together. The male portions 9 are of shorter length than the female portions 10 by a length difference corresponding to the axial extent of the lens 7 so as to prevent axial movement of the lens.

The lens 7 has a cylindrical surface 12 which is a sliding fit within the female portion 10 so that once in position the lens is maintained in axial alignment with the spacer 8 and the lens has end faces 13 and 14 which abut at their radial extremities with the shoulder 11 and the annular end surface 15 of the male portion 9 respectively. The lens 7 is thereby firmly clamped.

The shaft 2 also houses a fibre optic bundle 16 which occupies a duct 17 defined by the outer surface 18 of a window tube 19 and the inner surface 20 of the shaft 2. The window tube 19 extends along the length of and parallel to the shaft 2 and lies in contact with a side portion 21 of the shaft 2 such that the duct 17 is crescent shaped.

The optical assembly 7, 8 is itself a self supporting structure and is a sliding fit within the window tube 19 so that the optical assembly may readily be removed from the shaft without disturbing the fibre optic bundle. Such removal may be necessary for servicing the optical assembly or when it is desired to replace the outer components of the shaft whilst re-using the original optical assembly.

The window tube 19 has a window 22 which is aligned with the objective optical system 4 so that an object may be viewed through the window. The fibre optic bundle 16 terminates at the first end of the shaft 3 adjacent to the window 22 in a polished end surface 23 formed by bonding together the fibres with a suitable resin and polishing the solid mass thereby formed. The other end (not shown) of the fibre optic bundle 16 is connected to a light source (not shown) which may either be housed integrally with the eye piece 6 or housed separately in a housing connected to the borescope by a fibre optic link.

The borescope 1 is assembled by sliding a pre-cleaned first lens 7 into the female portion 10 of a pre-cleaned first spacer 8 and if necessary cleaning the internal portion of the spacer to remove any contamination caused by scraping during the sliding motion. A male portion 9 of a further spacer is coated with adhesive and inserted within the female portion 10 of the first spacer so as to firmly seat the lens against the shoulder 11. The further spacer is then internally cleaned and a further lens inserted in the female portion 10 of the further spacer. Further spacers and lenses are added in like manner until an optical assembly 7, 8 of the required length and optical properties is formed.

In use the shaft 2 of the borescope 1 is inserted through a bore and an object is illuminated by light from the light source passing through the fibre optic bundle 16 and emerging from the end surface 23. Light reflected from the object enters through the window 22 and is collected by the objective optical system 4 and relayed to the eye piece 6 by the optical assembly 7, 8 so that an image of the object may be viewed.

An alternative borescope 30 is shown in FIGS. 3 and 4 in which components common to the borescope 1 of FIGS. 1 and 2 are numbered with the same numerals. The borescope 30 similarily includes an optical assembly 7, 8 having interfitting male and female portions 9, 10 but does not include a window tube. The fibre optic bundle 16 is in this case contained within a sheath 31 of a flexible low friction material. The sheath 31 in a preferred embodiment is formed as a helically wound tape of polytetrafluorethylene which is wrapped around the fibres as a thin sheet. The fibre optic bundle 16 partially fills a duct 32 defined by the external surface 33 of the optical assembly 7, 8 and the internal surface 20 of the shaft 2. The optical assembly 7, 8 may be slid into or out of position in the shaft 2 by virtue of the low friction sheath 31 which confines the optical fibres in crescent shaped cross section whilst the optical assembly 7, 8 lies in contact with one side 21 of the shaft 2. The need for a window tube is therefore obviated so that compared with a conventional borescope a greater cross sectional area is available to be taken up by additional optical fibres 16 or a lens 7 of greater diameter supported in spacers 8 of correspondingly enlarged diameter.

A further borescope 40 is shown in FIGS. 5 and 6 in which those components which are common to borescopes 1 and 30 are correspondingly numbered.

The borescope 40 has a lens tube 41 containing lenses 7 which are spaced apart by tubular spacers 42. A fibre optic bundle 16 is contained within a flexible sheath 31 and partially fills a crescent shaped duct 43 defined by the external surface 44 of the lens tube 41 and the internal surface 20 of the shaft 2. The lens tube 41 lies in contact with one side 21 of the shaft 2 and may be inserted or removed by virtue of the low friction properties of the sheath 31. The need for a window tube is therefore obviated so that greater cross sectional area is available for additional optical fibres 16 or a lens tube of larger diameter enabling lenses 7 of greater diameter to be used.

The borescopes 1, 30 and 40 as described above are all of the lateral viewing type in which the direction of view of the objective optical system is at right angles to the longitudinal axis of the borescope. Alternative embodiments in accordance with the present invention may be constructed in which the direction of view is other than at right angles for example an on-axis borescope in which the direction of view extends forwardly along the longitudinal axis or a retro-viewing borescope in which the direction of view is directed rearwardly parallel to the borescope axis.

Further alternative embodiments of the borescope in accordance with the present invention are envisaged in which the lens may be replaced by more complex optical elements having multiple components and also in which the eye piece may be replaced by other imaging means such as a camera. Alternative embodiments are also envisaged in which the formations for connecting adjacent spacers interconnect by alternative means such as screw threaded connectors, bayonet fittings or any other alternative configuration which enables the optical assembly to be self supporting without the need for a surrounding lens tube.

I claim:

1. A borescope for use in through-bore inspection of inaccessible objects comprising a tubular shaft having a first end for insertion in use into a bore, objective means at the first end of the shaft for viewing an object, imaging means at the second end of the shaft, and optical relay means for relaying light from the objective means to the imaging means such that the object may be imaged by the imaging means wherein the relay means comprises an optical assembly in which a plurality of optical elements are spaced apart by tubular spacers through which the optical path extends, said spacers including formations for connecting adjacent spacers and for housing the optical elements such that the spacers and optical elements form a self-supporting assembly, said formations comprising male and female portions of each spacer, which portions interfit with cooperating portions of adjacent spacers, and wherein each optical element includes a cylindrical surface which is a sliding fit in axial alignment within a respective female portion.

2. A borescope as claimed in claim 1 wherein each spacer comprises a tube of substantially uniform wall thickness, the tube diameter being stepped at an annular shoulder such that a male portion is formed on one side of the shoulder and a female portion of larger diameter is formed on the other side of the shoulder, the external and internal diameters of the male and female portions respectively being such as to provide a sliding fit connection between cooperating portions of adjacent spacers.

3. A borescope as claimed in claim 1 and further comprising fibre optic means for conducting light along the shaft from a light source to the first end of the shaft to illuminate the object.

4. A borescope as claimed in claim 3 wherein the optical assembly is housed in a window tube having a window through which the objective means may view an object, wherein the optical assembly is a sliding fit within the window tube and the fibre optic means occupies a duct defined by the exterior surface of the window tube and the interior surface of the shaft.

5. A borescope as claimed in claim 4 wherein the window tube is in contact with one side of the shaft such that the duct is crescent shaped in cross section.

6. A borescope as claimed in claim 3 wherein the optical assembly is housed in the shaft and wherein the fibre optic means occupies a duct defined by the external surface of the optical assembly and the internal surface of the shaft, which fibre optic means comprises a bundle of optical fibres in a flexible sheath.

7. A borescope as claimed in claim 6 wherein the sheath is of a low friction material.

8. A method of assembling a borescope having an optical assembly in which a plurality of optical elements are spaced apart by tubular spacers through which the optical path extends, said spacers including formations for connecting adjacent spacers and for housing the optical elements such that the spacers and optical elements form a self-supporting assembly, said formations comprising male and female portions of each spacer, which portions interfit with cooperating portions of adjacent spacers, and wherein each optical element includes a cylindrical surface which is a sliding fit in axial alignment within a respective female portion, the method comprising the steps of fitting an optical element into a female portion of a first spacer, fitting a male portion of a further spacer into the female portion of the first spacer together with an adhesive layer therebetween, fitting a further optical element into the female portion of the further spacer and adding additional further spacers and optical elements in like manner as required to form said optical assembly.

9. A method of assembling a borescope of as claimed in claim 8 and including the further steps of cleaning each spacer internally before each step of fitting an optical element or further spacer therein.

* * * * *